United States Patent [19]

Ambrus et al.

[11] 4,052,407
[45] Oct. 4, 1977

[54] THIAZOLE DERIVATIVES AND PROCESSES FOR PREPARING THE SAME

[75] Inventors: Gabor Ambrus; Istvan Barta; Zsuzsanna Mehesfalvi, nee Vajna; Gyula Horvath, all of Budapest, Hungary

[73] Assignee: Gyogyszerkutato Intezet, Budapest, Hungary

[21] Appl. No.: 577,348

[22] Filed: May 14, 1975

[30] Foreign Application Priority Data

May 14, 1974 Hungary .............................. GA 1269

[51] Int. Cl.² .......................................... C07D 277/20
[52] U.S. Cl. .................................. 260/302 R; 424/270
[58] Field of Search .................................... 260/302 R

[56] References Cited

U.S. PATENT DOCUMENTS 3,846,475  11/1974  Crabbe et al. ................... 260/302 R

*Primary Examiner*—R. J. Gallagher
*Attorney, Agent, or Firm*—Young & Thompson

[57] ABSTRACT

Novel thiazole derivatives of the formula

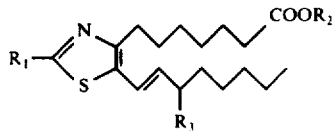

wherein $R_1$ and $R_2$ are hydrogen or methyl, $R_3$ is oxo, hydroxyl or acetoxy, have prostaglandin side chains and have an action that is more selective than that of natural prostaglandins. They inhibit the activity of enzymes inducing the decomposition of prostaglandins in the organism and thus they increase the endogenous level of prostaglandins. Various novel methods are provided for their production.

14 Claims, 1 Drawing Figure

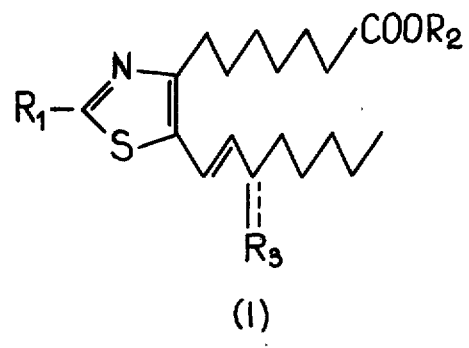
(I)
REACTION SCHEME 1
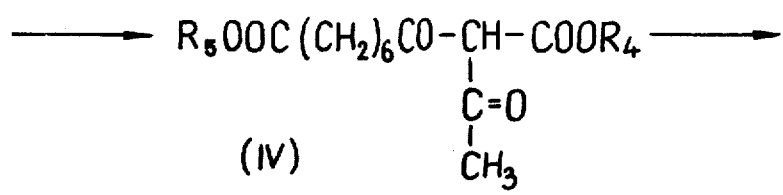
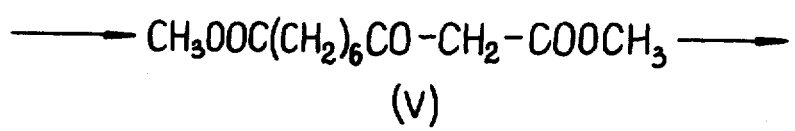
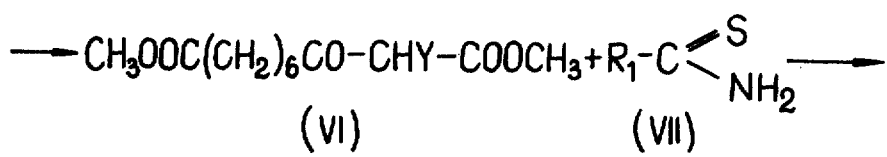

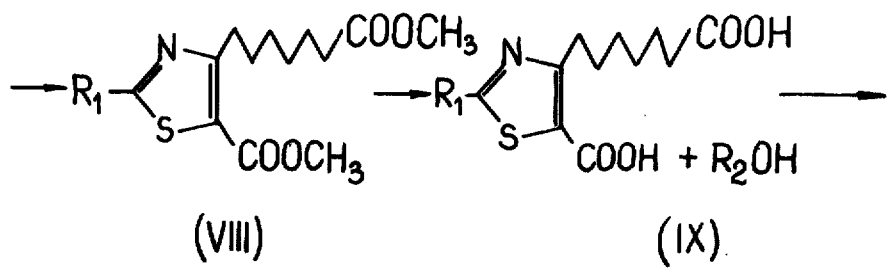
(VIII)          (IX)
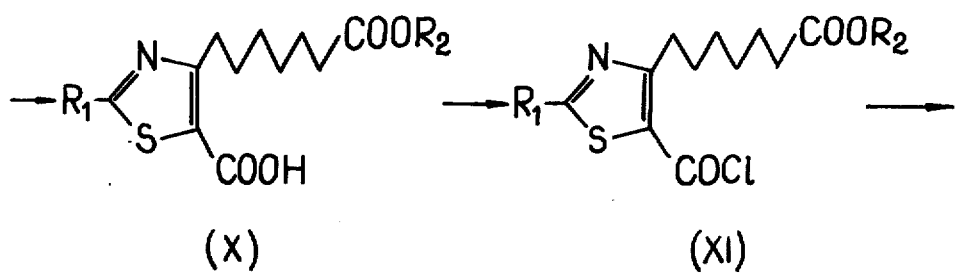
(X)          (XI)
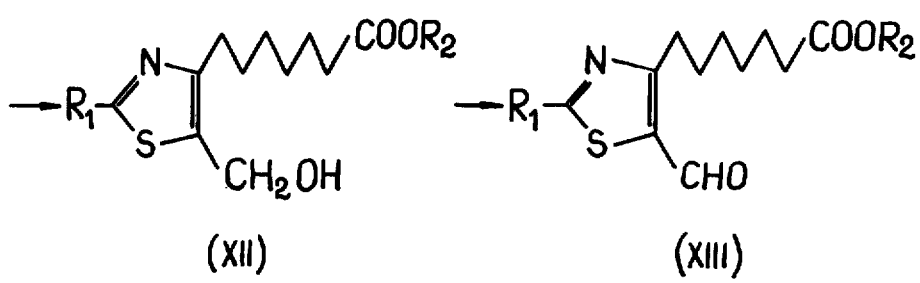
(XII)          (XIII)
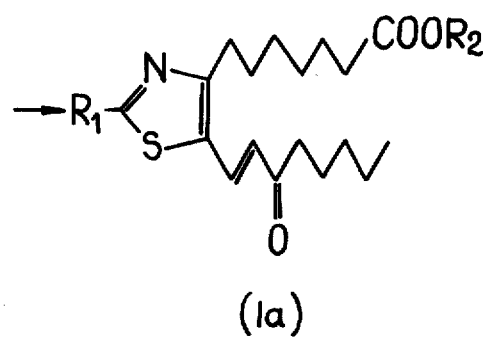
(Ia)

REACTION SCHEME 2
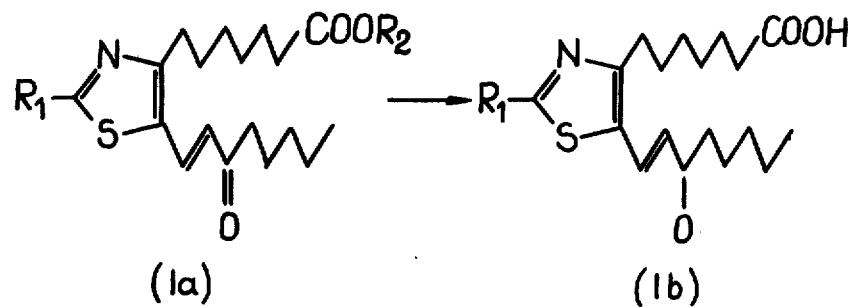
REACTION SCHEME 3
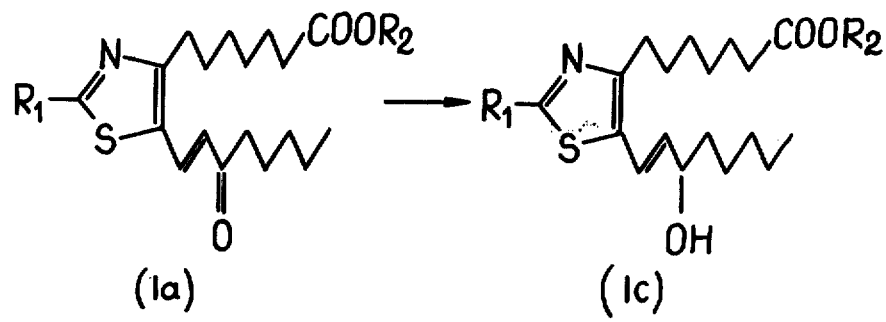
REACTION SCHEME 4
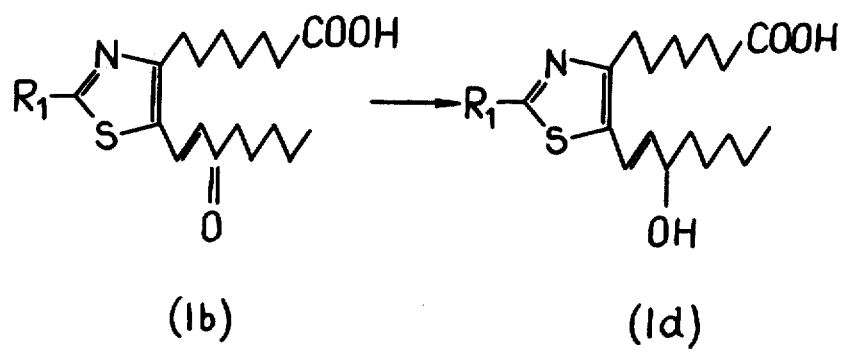

REACTION SCHEME 5
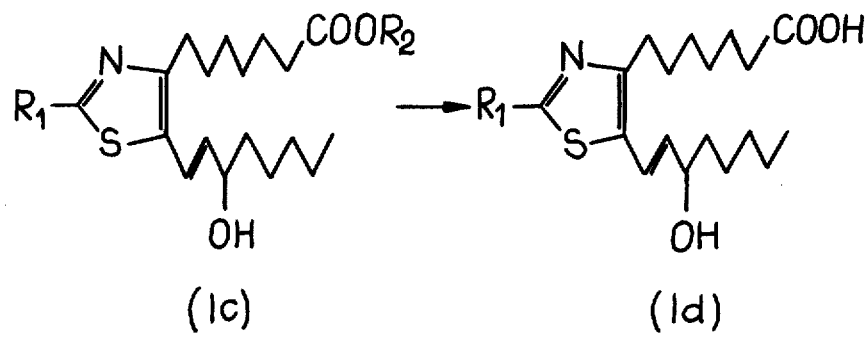
REACTION SCHEME 6
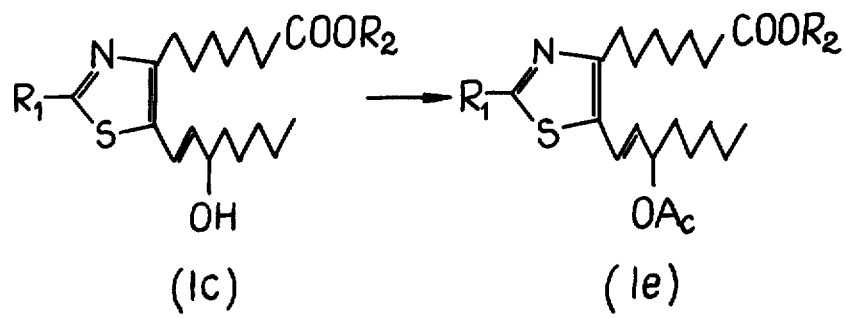

THIAZOLE DERIVATIVES AND PROCESSES FOR PREPARING THE SAME

The invention relates to novel thiazole derivatives of the general formula I, carrying prostaglandin sidechains,

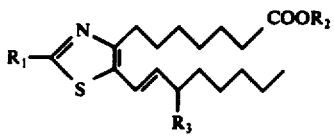

(I)

wherein $R_1$ and $R_2$ denote hydrogen atoms or alkyl groups, and $R_3$ denotes an oxo, hydroxyl or acyloxy group. Furthermore the invention relates to processes for preparing these compounds.

Attempts are known to utilize the various physiological effects of protaglandins in several fields or pharmaceutical research. The effect of native prostaglandins is not sufficiently selective, and they are quickly inactivated in the organism. These drawbacks can be eliminated by the preparation of prostaglandin analogues which have a more selective effect and are metabolized slower (P. Ramwell and J. Shaw; Ann. N. Y. Acad. Sci. 180, 10 /1971/). Among the compounds structurally related to the prostaglandins also compounds can be found which inhibit both the biosynthesis and various effects of endogenous prostaglandins (J. Fried et. al.: Ann. N. Y. Acad. Sci. 180, 38 1971/). Some of these compounds may be valuable from therapeutic aspects. Compounds inhibiting the metabolization of natural prostaglandins are also of a therapeutic significance.

The invention is aimed at preparation of novel compounds with a structure related to that of prostaglandins, compounds in which the prostaglandin side-chains are coupled to a thiazole ring, instead of to the cyclopentane ring present in natural prostaglandins. These two side-chains can be located vicinally at the carbon atoms 4 and 5 of the thiazole ring.

In the course of our experiments we succeeded in synthesizing new thiazole derivatives in which a 6-carboxyhexyl or 6-carbalkoxyhexyl side chain is coupled to the $C_4$-atom of the thiazole ring, a 3-oxo-1-trans-octenyl or 3-hydroxy-1-trans-octenyl or 3-acyloxy-1-trans-octenyl side-chain is coupled to the $C_5$-atom of the ring, and a hydrogen atom or an alkyl group is coupled to the $C_2$-atom of the ring.

In one aspect the invention provides new thiazole derivatives of the general formula I

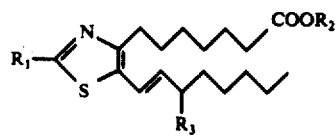

(I)

wherein $R_1$ and $R_2$ denote hydrogen atoms or alkyl groups, and $R_3$ denotes an oxo, hydroxyl or acyloxy group.

Compounds of the general formula I produced according to the invention have been classified as follows:

|    | $R_1$            | $R_2$    | $R_3$    |
|----|------------------|----------|----------|
| Ia | hydrogen or alkyl | alkyl    | oxo      |
| Ib | "                | hydrogen | oxo      |
| Ic | "                | alkyl    | hydroxyl |
| Id | "                | hydrogen | hydroxyl |
| Ie | "                | alkyl    | acyloxy  |

In an other aspect the invention provides methods for preparing the new compound of general formula I.

Method (a) (reaction scheme 1) comprises the following steps: acylating the sodium derivative of an acetoacetic acid alkylester of the general formula II, wherein $R_4$ denotes an alkyl group, with a 7-carbalkoxyheptanoyl chloride of the general formula III, wherein $R_5$ denotes an alkyl group, and converting the obtained 10-carbalkoxy-2,4-diketodecane-3-carboxylic acid alkylester of the general formula IV, wherein $R_4$ and $R_5$ have the same meanings as above, with a methanolic solution of sodium methoxide into 9-carbomethoxy-3-ketononanoic acid methylester of formula V, halogenating the latter compound to 9-carbomethoxy-2-halo-3-ketononanoic acid methylester of the general formula VI, wherein Y denotes a halogen atom, reacting VI with a thioacid amide of the general formula VII, wherein $R_1$ denotes a hydrogen atom or an alkyl group, hydrolyzing the obtained 4-(6-carbomethoxyhexyl)-thiazole-5-carboxylic acid methylester of the general formula VIII, wherein $R_1$ stands for a hydrogen atom or an alkyl group, to obtain 4-(6-carboxyhexyl)-thiazole-5-carboxylic acid of the general formula IX, wherein $R_1$ is a hydrogen atom or an alkyl group, subjecting IX to selective esterification with an alcohol of the general formula $R_2OH$, wherein $R_2$ stands for an alkyl group, in the presence of p-toluenesulphonic acid, converting the thus- obtained 4-(6-carbalkoxyhexyl)-thiazole-5-carboxylic acid of the general formula X, wherein $R_1$ is a hydrogen atom or an alkyl group and $R_2$ is an alkyl group, into 4-(6-carbalkoxyhexyl)-thiazole-5-carboxylic acid chloride of the general formula XI, wherein $R_1$ is a hydrogen atom or an alkyl group and $R_2$ is an alkyl group, reducing XI with an alkali metal borohydride to 4-(6-carbalkoxyhexyl)-5-hydroxymethylthiazole of the general formula XII, wherein $R_1$ is a hydrogen atom or an alkyl group and $R_2$ is an alkyl group, then oxidizing XII to 4-(6-carbalkoxyhexyl)-thiazole-5-carbaldehyde of the general formula XIII, wherein $R_1$ is a hydrogen atom or an alkyl group, and $R_2$ is an alkyl group, reacting XIII with 2-oxo-heptylidene-triphenylphosphorane to obtain 4-(6-carbalkoxyhexyl)-5-(3-keto-1-trans-octenyl)-thiazole of the general formula Ia, wherein $R_1$ is a hydrogen atom or an alkyl group and $R_2$ is an alkyl group.

Method (b) comprises the steps of reducing 4-(6carbalkoxyhexyl)-thiazole-5-carboxylic acid chloride of the general formula XI, wherein $R_1$ stands for a hydrogen atom or an alkyl group and $R_2$ stands for an alkyl group, with lithium tri-tert.-butoxy-aluminium hydride to 4-(6-carbalkoxyhexyl)-thiazole-5-carbaldehyde of the general formula XIII, wherein $R_1$ stands for a hydrogen atom or an alkyl group and $R_2$ stands for an alkyl group, then reacting XIII with 2-oxo-heptylidene-triphenylphosphorane to obtain 4-(6-carbalkoxyhexyl)-5-(3-keto-1-trans-octenyl)-thiazole of the general formula Ia, wherein $R_1$ is a hydrogen atom or an alkyl group and $R_2$ is an alkyl group.

Method (c) comprises the steps of converting 4-(6-carbalkoxyhexyl)-thiazole-5-carbaldehyde of the general formula XIII, wherein $R_1$ is a hydrogen atom or an alkyl group, and $R_2$ is an alkyl group, with the sodium derivative of 2-oxo-heptylphosphonic acid dimethylester or with 2-oxo-heptylidene-triphenyl phosphorane into 4-(6-carbalkoxyhexyl)-5-(3-keto-1-trans-octenyl)-thiazole of the general formula Ia, wherein $R_1$ is a hydrogen atom or an alkyl group and $R_2$ is an alkyl group, and, if desired, hydrozyling Ia to 4-(6-carboxyhexyl)-5-(3-keto-1-transoctenyl)-thiazole of the general formula Ib, wherein $R_1$ is a hydrogen atom or an alkyl group (reaction scheme 2), or, if desired, reducing Ia with an alkali metal borohydride to 4-(6-carbalkoxyhexyl)-5-(3-hydroxy-1-trans-octenyl)-thiazole of the general formula Ic, wherein $R_1$ is a hydrogen atom or an alkyl group and $R_2$ is an alkyl group (reaction scheme 3), or, if desired, reducing the compound of general formula Ib with an alkali metal borohydride (reaction scheme 4), or hydrolyzing the compound of the general formula Ic (reaction scheme 5) to 4-(6-carboxyhexyl)-5-(3-hydroxy-1-trans-octenyl)-thiazole of the general formula Id, wherein $R_1$ stands for a hydrogen atom or an alkyl group, or acylating the compound of the general formula Ic (reaction scheme 6) to 4-(6-carbalkoxyhexyl(-5-(3-acyloxy-1-trans-octenyl)-thiazole of the general formula Ie, wherein $R_1$ stands for a hydrogen atom or an alkyl group and $R_2$ stands for an alkyl group.

In method (a) for synthesising the compounds of the general formula I the starting materials are an acetoacetic alkylester of the general formula II, preferably the readily available acetoacetic acid ethylester, and suberic acid (hexane-1,6-dicarboxylic acid).

The acetoacetic acid ester is converted into its sodium derivative by stirring the ester for 3-5 hours with sodium metal cut to small pieces, in a medium of anhydrous benzene or anhydrous ether. When reacting the sodium derivative of the acetoacetic acid ester with 7-carbalkoxyheptanoyl chloride of the general formula III prepared from suberic acid, a 10-carbalkoxy-2,4-diketo-decane-3-carboxylic acid alkylester of the general formula IV is obtained. The 7-carbalkoxy-heptanoyl chloride of the general formula III is prepared by producing a semiester from suberic acid in the known way, and then heating the obtained 7-carbalkoxyheptanoic acid with thionyl chloride until the acid chloride of the general formula III is formed. For the preparation of the compound of the general formula IV expediently 7-carbomethoxyheptanoyl chloride, a known compound (J. Am. Chem. Soc. 78, 2451 /1956/) is used. The 10-carbalkoxy-2,4-diketodecane-3-carboxylic acid alkylester of the general formula IV is prepared by producing the sodium derivative of the acetoacetic acid alkylester of the general formula II and adding a 7-carbalkoxyheptanoyl chloride of the general formula III immediately to the reaction mixture. When purifying the crude product it is of advantage to observe that on treating a 10-carbalkoxy-2,4-diketodecane-3-carboxylic acid alkylester of the general formula IV with a saturated solution of potassium carbonate or a saturated sodium carbonate solution according to the method of S. Archer and M. G. Pratt (J. Am. Chem. Soc. 66, 1656 /1944/), an alkali metal derivative isolable from the by-products formed at the formation of the compound of the general formula IV can be produced. However, the purification of the crude product is not needed since the crude product can be used directly for the preparation of 9-carbomethoxy-3-ketononanoic acid methylester of the formula V.

The 10-carbalkoxy-2,4-diketodecane-3-carboxylic acid alkylester of the general formula IV is converted at room temperature by a methanolic solution of sodium methoxide, into 9-carbomethoxy-3-ketononanoic acid methylester of formula V. The crude product obtained in this reaction can be purified by fractional distillation.

The 9-carbomethoxy-3-ketononanoic acid methylester of formula V can be readily halogenated at the $C_2$ atom situated between the keto group and the carbomethoxy group. Chlorination in medium carbon tetrachloride medium with 1.0-1.2 moles of sulphuryl chloride proved to be favourable.

On reacting the halogenated product, 9-carbomethoxy-2-halo-3-ketononanoic acid methylester of the general formula VI with thioacid amides of the general formula VII, 4-(6-carbomethoxyhexyl)-thiazole-5-carboxylic acid methylester of the general formula VIII which carries hydrogen atom or an alkyl group on $C_2$ is obtained. Thiazole formation is completed in one hour when the 9-carbomethoxy-2-chloro-3-ketononanic acid methylester of formula VI is refluxed in methanol with 1.0-1.2 moles of a thioacid amide of the general formula VII. On subjecting the crude product, obtained by the extracting the reaction mixture neutralized with sodium carbonate solution with ether, to purification by column chromatography or preparative thin layer chromatography, an analytically pure compound of the general formula VIII can be obtained.

The 4-(6-carboxyhexyl)-thiazole-5-carboxylic acid of the general formula IX, which carries a hydrogen atom or an alkyl group on $C_2$, can preferably be prepared by the direct hydrolysis of the crude product compound of the general formula VIII. Hydrolysis is carried out preferably with an alkali hydroxide. Saponification with 2.5-3.5 moles of sodium hydroxide is completed in an ethanolic-aqueous medium at boiling temperature in 0.5-1.0 hour. The product of saponification, that is the 4-(6-carboxyhexyl)-thiazole-5-carboxylic acid of the general formula IX, which carries a hydrogen atom or an alkyl group on $C_2$, is purified by recrystallization.

On investigating the possibility of the selective esterification of the carboxyl group located in the ring and in terminal position of the chain of the compound of the general formula IX it has been found that esterification with aliphatic alcohols in the presence of p-toluene-sulphonic acid as catalyst takes place at room temperature only at the terminal carboxyl group. This finding is essential from the aspect of the synthesis. Namely, the free carboxyl group located in the ring of the 4-(6-carbalkoxyhexyl)-thiazole-5-carboxylic acid of the general formula X, which carries a hydrogen atom or an alkyl group on $C_2$ and which possesses a protected terminal carboxyl group can be converted into an acid chloride in a selective way.

The acid chloride of the general formula XI is produced by reacting the compound of the general formula X expediently with oxalyl chloride in a benzene at room temperature. However, other known methods for the preparation of acid chlorides can also be applied.

The 4-(6-carbalkoxyhexyl)-5-hydroxymethyl thiazole of the general formula XII which carries a hydrogen atom or an alkyl group on $C_2$ is obtained by reducing an acid chloride of the general formula XI with an alkali metal borohydride. Reduction is carried out expediently in dioxane with 1.5-2.0 moles of sodium borohydride.

The 4-(6-carbalkoxyhexyl)-thiazole-5-carbaldehyde of the general formula XIII carries a hydrogen atom or an alkyl group on $C_2$ is produced by mild oxidation of the hydroxyl group of the compound of the general formula XII. A very favourable way of carrying out this oxidation is the method of Collins et al. (Tetrahedron Letters 1968, 3363), using chromium trioxide-pyridine complex in dichloromethane.

The 4-(6-carbalkoxyhexyl)-5-(3-keto-1-trans-octenyl)-thiazole of the general formula Ia which carries a hydrogen atom or an alkyl group on $C_2$ is prepared by Wittig reaction from the compound of the general formula XIII. 2-oxo-heptylidene triphenyl phosphorane prepared in the way described by M.P.L. Caton et al. (Tetrahedron Letters 1972, 773) can be favourably applied as Wittig reagent. The compound of the general formula XIII is converted by 2.5 moles of 2-oxo-heptylidene triphenyl phosphorane under stirring at room temperature in 16 hours into a compound of the general formula Ia which can be separated from the triphenyl-phosphine oxide formed in the reaction and from the residual excess of 2-oxo-heptylidene triphenyl phosphorane by column chromatography or by preparative thin layer chromatography.

According to method (b), 4-(6-carbalkoxyhexyl)-thiazole-5-carbaldehyde of the general formula XIII, which carries a hydrogen atom or an alkyl group on $C_2$, is prepared directly from the acid chloride of the general formula XI by reduction with lithium tri-tert.-butoxy-aluminium hydride. This reduction is carried out expediently in anhydrous tetrahydrofuran at $-50°$ C.

According to method (c), 4-(6-carbalkoxyhexyl)-thiazole-5-carbaldehyde of the general formula XIII, which carries a hydrogen atom or an alkyl group on $C_2$, is converted into 4-(6-carbalkoxyhexyl)-5-(3-keto-1-trans-octenyl)-thiazole of the general formula Ia, which carries a hydrogen atom or an alkyl group on $C_2$, by reacting with the sodium derivative of 2-oxo-heptylphosphonic acid dimethylester. The latter compound can be obtained in the way described by E. J. Corey et al. (J. Am. Chem. Soc. 90, 3247 /1968/).

The 4-(6-carboxyhexyl)-5-(3-keto-1-trans-octenyl)-thiazole of the general formula Ib, which carries a hydrogen atom or an alkyl group on $C_2$, is obtained by the hydrolysis of the corresponding compound of formula Ia. According to our investigations enzymatic hydrolysis is more favourable than chemical methods. It proved to be of advantage to apply esterase enzymes of microbiological origin, e.g. the lipase enzyme produced by the fungus Rhizopus oryzae and prepared according to Hungarian Patent Specification No. 160,109, for the hydrolysis of the compound of the general formula Ia. The enzymatic hydrolysis can be preferably carried out in a phosphate buffer of pH 7.5. To improve the dispersibility of the compound to be hydrolyzed it is advantageous to add gum arabic and the sodium salt of taurocholic acid to the reaction mixture. The ester group of the compound of the general formula Ia can be saponified also with an alkali hydroxide. However, some decomposition occurs even under mild conditions that is when the reaction is carried out at room temperature under nitrogen atmosphere. Consequently, the yield is lower than that of the enzymatic hydrolysis.

The 4-(6-carbalkoxyhexyl)-5-(3-hydroxy-1-trans-octenyl)-thiazole of the general formula Ic, which carries a hydrogen or an alkyl group on $C_2$, can be prepared from the corresponding compound of general formula Ia by reduction with an alkali metal borohydride. The ketone group of the compound of the general formula Ia is reduced in an aqueous-propanolic medium by 0.5 mole of sodium borohydride at room temperature in 2 hours.

The 4-(6-carboxyhexyl)-5-(3-hydroxy-1-trans-octenyl)-thiazole of the general formula Id, which carries a hydrogen or an alkyl group on $C_2$, is obtained by reducing the corresponding compound of general formula Ib with an alkali metal borohydride. This reaction proceeds slower than the reduction of the compound of the general formula Ia; it requires at room temperature in an aqueous isopropanonolic medium even in the presence of 2 moles of sodium borohydride about 16 hours. The compound of the general formula Id can be produced more favourably by the enzymatic hydrolysis of the corresponding compound of general formula Ic. The enzymatic hydrolysis is carried out in the way already specified at the hydrolysis of the compound of the general formula Ia.

The 4-(6-carbalkoxyhexyl)-5-(3-acyloxy-1-transoctenyl)-thiazole of the general formula Ie, which carries a hydrogen atom or an alkyl group on $C_2$, is prepared by esterification of the hydroxyl group of the corresponding compound of general formula Ic. Esterification can be carried out by known methods, such as treatment with acid anhydrides or acid chlorides, as well. The hydroxyl group can be esterified under mild conditions, e.g. it can be acetylated in a pyridine at room temperature with acetic anhydride.

The structure of the compounds produced by the process according to the invention is unequivocally confirmed by the data of the IR, NMR and mass spectra specified in the following Examples.

On investigating the biological properties of the compounds of the general formula I prepared according to the invention it has been found that they have prostaglandin-like effects on certain organs. From the aspect of therapeutic application it is essential that their action is more selective than that of natural prostaglandins. They possess the valuable property of inhibiting the activity of enzymes inducing the decomposition of prostaglandins in the organism and thus they increase the endogenous level of prostaglandins.

To illustrate the prostaglandin-like effect of the compounds of general formula I the effects of 4-(6-carboxyhexyl)-5-(3-hydroxy-1-trans-octenyl)-thiazole (Id, $R_1$ = H) on rat uterus and on rat fat tissue are described. Muscle contractions were measured by the method of W. H. Newton (J. Physiol. (London) 79, 301/1933/) whereas lipolysis appearing in the fat tissue was measured by the method of G. Cseh et al. (Acta Biochim. Biophys. Acad. Sci. Hung. 8, 245 /1973/).

a. The compound used in a concentration of 0.01 µg/ml induced the contraction of rat uterus suspended in a Krebs-Ringer solution containing 0.2% of glycose which exhibited no spontaneous contractions.

b. The compound in concentrations above 0.1 µg/ml increased, as a function of the concentration, the size and frequency of the rhythmical contractions of rat uterus suspended in the physiological nutrient solution specified under point (a).

c. From the aspect of the effect on the uterus the compound exhibited synergism with prostaglandins.

d. On applying the compound in a concentration of 0.001 µg/ml it decreased the lipolysis of the epididymal fat tissue of rats induced by 0.01 µg/ml of isopropylnoradrenalin.

It has been observed further that the activity of the enzyme 15-hydroxyprostaglandin dehydrogenase responsible for the inactivation of natural prostaglandins is competitively inhibited by the compounds of formula Ib and Id, such as 4-(6-carboxyhexyl)-5-(3-keto-1-transoctenyl)-thiazole and 4-(6-carboxyhexyl)-5-(3-hydroxy-1-trans-octenyl)-thiazole. In accordance with this observation it has been experienced that the prostaglandin content of the rat uterine horn incubated at 37° C in a Krebs-Ringer solution of 0.2% glucose content is significantly increased by adding 4-(6-carboxyhexyl)-5-(3-hydroxy-1-trans-octenyl)-thiazole (Id, $R_1$ = H) to the solution. The effect of the investigated compounds on 15-hydroxyprostaglandin dehydrogenase was determined by the method of M. A. Marrazzi and F. M. Matschinsky (Prostaglandins 1, 373 /1972/), whereas the prostaglandin content of rat uterus by the method of N. Gilmore et al. (Nature 218, 1135 /1968/).

The process according to the invention is further illustrated by the following non-limiting Examples.

EXAMPLE 1

Preparation of 4(6-carbomethoxyhexyl)-5-(3-keto-1-trans-octenyl)-thiazole (Ia, $R_1$ = H)

a. 10 Carbomethoxy-2,4diketodecane-3-carboxylic acid ethylester (IV)

Small portions of 3.45 g of metallic sodium cut to pieces were added in 2 hours under stirring to a solution of 19.5 g of acetoacetic acid ethylester (II) in 250 ml of anhydrous benzene, then stirring was continued for another 3 hours until the reaction with sodium was completed. The obtained suspension was treated under stirring with 31 g of 7-carbomethoxyheptanoyl chloride (III) added dropwise in 30 minutes. Subsequently the reaction mixture was stirred for further 30 minutes and refluxed for 15 minutes. After cooling, the reaction mixture was poured onto an icy 10 % sulphuric acid solution. The benzene phase of the acidified reaction mixture was separated, washed with water to neutral and dried over sodium sulphate. On removing benzene by vacuum distillation, 44.5 g of a crude product containing 10-carbomethoxy-2,4-diketodecane-3-carboxylic acid ethylester (IV) were obtained which could be used without further purification for the preparation of 9-carbomethoxy-3-ketononanoic acid methylester (V) according to point (b).

10-Carbomethoxy-2,4-diketodecane-3-carboxylic acid ethylester (IV) of analytical purity was prepared as follows. The solution of 10 g of the crude product in 40 ml of diethyl ether was shaken with 40 ml of saturated potassium carbonate solution. The potassium derivative of 10-carbomethoxy-2,4-diketodecane-3-carboxylic acid ethylester gave a separate layer between the ethereal and the aqueous phases. After separating this oil it was acidified with a 10% sulphuric acid solution and the obtained solution extracted with diethyl ether. The ethereal extract was washed with water to neutral and dried over sodium sulphate. On removing ether by vacuum distillation 6.5 g of a distilltion residue containing 10-carbomethoxy-2,4-diketodecane-3-carboxylic acid ethylester (IV) were obtained. This residue was purified by preparative thin layer chromatography on a silica gel layer with the use of a running solvent mixture of 40% ethyl acetate and 60% n-heptane.

IR spectrum (film): $\nu$ CH 2990-2860, $\nu$ C=O 1735, 1705, $\nu$ C-O 1240 cm$^{-1}$.

NMR spectrum (CCl$_4$): $\delta$ OCH$_2$ 4.38, 4.15 (2 H, q, J = 7.5 Hz), $\delta$ OCH$_3$ 3.62 (3 H, s), $\delta$ CH$_2$(C=O) 2.67 (2 H, t, J = 7 Hz), 2.28 (2 H, t, J = 7 Hz), $\delta$ CH$_3$(C=O) 2.32 (3 H, s), $\delta$ CH$_2$ 1.9-1.25 (8 H, m), $\delta$ CH$_3$ 1.35 (3 H, t, J = 7.5 Hz) ppm.

b. 9-Carbomethoxy-3-ketonananoic acid methylester (V)

A solution of sodium methoxide prepared from 3.45 g of sodium and 100 ml of anhydrous methanol was added to 44.5 g of the crude product of 10-carbomethoxy-2,4-diketodecane-3-carboxylic acid ethylester (IV). The reaction mixture was allowed to stand 16 hours at room temperature, then poured onto an icy 10% sulphuric acid solution. The acidified aqueous reaction mixture was extracted with diethyl ether, the ethereal extract was dried over sodium sulphate, then ether was removed by evaporation. On subjecting the obtained distillation residue to fractional distillation, 22.5 g of 9-carbomethoxy-3ketonononic acid methylester (V) were obtained. B.p.: 160° C at 0.4 torr.

IR spectrum (film): $\nu$ CH 2980-2860, $\nu$ C=O 1732, $\nu$ C-O 1250 cm$^{-1}$.

NMR spectrum (CCl$_4$): $\delta$ OCH$_3$ 3.7 (3H, s), 3.62 (3 H, s), $\delta$ CH$_2$(C=O) 3.35 (2 H, s), 2.6-2.0 (4 H, m), $\delta$ CH$_2$ 1.9-1.2 (8 H, m) ppm.

c. 9-Carbomethoxy-2-chloro-3ketonononoic acid methylester (VI)

The solution of 22.2 g of 9-carbomethoxy-3ketonononoic acid methylester (V) in 20 ml of carbon tetrachloride was cooled to −5° C and the solution of 14.7 g of sulphuryl chloride in 10 ml of carbon tetrachloride was added dropwise to the solution. The reaction mixture was stirred for 30 minutes at −5° C, then for 30 minutes at room temperature and finally for 30 minutes at 60° C. After cooling, the reaction mixture was diluted with 100 ml of diethyl ether, then was washed with a 5% solution of sodium hydrogen carbonate and finally with water. On removing the solvent by distillation, 22.6 g of crude 9-carbomethoxy-2-chloro-3-ketonononoic acid methylester (VI) were obtained which could be used without any further purification for the preparation of 4-(6-carbomethoxy hexyl)-thiazole-5-carboxylic acid methylester (VIII, $R_1$ = H) according to point d). The fractional distillation of the crude product yielded 17 g of 9-carbomethoxy-2-chloro-3ketononanic acid methylester (VI) of analytical purity. B.p.: 155° C at 0.3 torr.

IR spectrum (film): $\nu$ CH 3000-2860, $\nu$ C=O 1735, $\nu$ C-O 1255 cm$^{-1}$.

NMR spectrum (CCl$_4$): $\delta$ C(Cl) 4.7 (1 H, s), $\delta$OCH$_3$ 3.8 (3 H, s), 3.6 (3 H, s), $\delta$ CH$_2$(C=O 2.68 (2 H, t, J = 7 Hz), 2.25 (2 H, t, J = 7 Hz), $\delta$ CH$_2$ 1.9-1.1 (8 H, m) ppm.

d. 6-carbomethoxyhexyl)-thiazole-5-carboxylic acid methylester (VIII, $R_1$ = H)

16.8 g of 9-carbomethoxy-2-chloro-3ketonononoic acid methylester (VI) and 4.5 of thioformamide (VII, $R_1$ = H) were refluxed in 90 ml of methanol for 1 hour, then methanol was evaporated in vacuo, and the distillation residue was dissolved in 150 ml of 2 N hydrochloric acid. The obtained solution was neutralized with a 5% solution of sodium carbonate, saturated with ammonium sulphate and extracted with 3 × 150 ml of diethyl ether. The ethereal extract was dried over sodium sulphate, then ether was evaporated. Thus 16 g of crude 4-(6-carbomethoxyhexyl)-thiazole-5-carboxylic acid methylester (VIII, $R_1$ = H) were obtained which could be used without any further purification for the preparation of 4-(6-carboxyhexyl)-thiazole-5-carboxylic acid (IX, $R_1$ = H) according to point (e).

On subjecting the crude product to purification by preparative thin layer chromatography on a silica gel layer using a mixture of 60% ethyl acetate and 40% n-heptane as running solvent, 4-(6-carbomethoxyhexyl)-thiazole-5-carboxylic acid methylester (VIII, $R_1$ = H) of analytical purity was obtained.

IR spectrum (film): $\nu$ CH 3000–2860, $\nu$ C=O 1740, 1715, $\nu$ C-O 1270 cm$^{-1}$.

NMR spectrum (CCl$_4$): $\delta \leq$ CH(thiazole) 8.7 (1 H, s), $\delta$OCH$_3$ 3.85 (3 H, s), 3.6 (3 H, s), $\delta$ CH$_2$ (vicinal to the ring) 3.15 (2 H, t, J = 7 Hz), $\delta$ CH$_2$(C=O) 2.25 (2 H, t, J = 7 Hz), $\delta$ CH$_2$ 1.95–1.1 (8 H, m) ppm.

e. 4-(6-Carboxyhexyl)-thiazole-5-carboxylic acid (IX, $R_1$ = H)

To the solution of 16 g of crude 4-(6carbomethoxyhexyl)-thiazole-5-carboxylic acid methylester (VIII, $R_1$ = H) in 50 ml of ethanol 100 ml of 2 N sodium hydroxide solution was added, the reaction mixture was refluxed for 30 minutes, then acidified with 5 N sulphuric acid under ice-cooling. On extracting the aqueous reaction mixture with 3 × 150 of ml ethyl acetate, the extract was dried over sodium sulphate and evaporated in vacuo. Recrystallization of the obtained crude product from diethylether afforded 9.4 g of 4-(6-carboxyhexyl)-thiazole-5carboxylic acid (IX, $R_1$ = H). M.p.: 151°–153° C.

IR spectrum (KBr): $\nu \leq$ CH 3080, $\nu$ CH 2980–2860, $\nu$C=O 1720 cm$^{-1}$.

NMR spectrum (CDCl$_3$ + DMSO-d$_6$): $\delta \leq$ CH (thiazole) 8.85 (1 H, s) $\delta$ COOH 8.65 (2 H), $\delta$CH$_2$ (vicinal to the ring) 3.2 (2 H, t, J = 7 Hz,) $\delta$ CH$_2$(C=O) 2.25 (2 H, t, J = 7 Hz), $\delta$CH$_2$ 1.95 - 1.0 (8 H, m) ppm.

f. 4(6-Carbomethoxyhexyl)-thiazole-5carboxylic acid (x, $R_1$ = H)

9.2 g of 4-(6carboxyhexyl)-thiazole-5-carboxylic acid (IX, $R_1$ = H) and 10.2 g of p-toluenesulphonic acid monohydrate were dissolved in 400 ml of methanol. The obtained reaction mixture was stirred for 2 hours at room temperature, then poured onto one liter of water. After saturating the aqueous solution with ammonium sulphate it was extracted with 3 × 400 ml of ethyl acetate, then the ethyl acetate extract was washed with water, dried over sodium sulphate and evaporated in vacuo. Recrystallization of the obtained crude product from a mixture of diethyl ether and n-hexane afforded 7.9 of 4-(6-carbomethoxyhexyl)-thiazole-5-carboxylic acid (X, $R_1$ =H). M.p.: 113°–114° C.

IR spectrum (KBr): $\delta \leq$ CH 3090, $\delta$ CH 3000–2860, $\delta$C=O 1730, 1705, $\delta$C-O 1260 cm$^{-1}$.

NMR spectrum (CDCl$_3$): $\delta$COOH 11.45 (1 H), $\delta \leq$ CH (thiazole) 9.0 (1 H, s), $\delta$ OCH$_3$ 3.65 (3 H. s), $\delta$ CH$_2$ (vicinal to the ring) 3.25 (2 H, t, J = 7.5 Hz), $\delta$ CH$_2$(C=O) 2.3 (2 H, t, J = 7 Hz), $\delta$ CH$_2$ 2.0–1.15 (8 H, m) ppm.

g. 4-(6-Carbomethoxyhexyl)-5-hydroxymethyl-thiazole (XII, $R_1$ = H).

To the solution of 7.75 g of 4-(6-carbomethoxyhexyl)-thiazole-5carboxylic acid (X, $R_1$ = H) in 100 ml of anhydrous benzene 8 ml of oxalyl chloride were added dropwise and the reaction mixture was allowed to stand overnight at room temperature, then the benzene and the excess oxalyl chloride were evaporated in vacuo. The obtained evaporation residue containing 4-(6-carbomethoxyhexyl)-thiazole-5-carboxylic acid chloride (XI, $R_1$ = H) was dissolved in 20 ml of anhydrous dioxane and the obtained solution was added dropwise, under stirring, to a suspension of 2.14 g of sodium borohydride in 40 ml of anhydrous dioxane. The stirring of the reaction mixture was continued for 30 minutes at room temperature and then for further 30 minutes at 80° C. When the reaction mixture cooled to room temperature, 50 ml of water were dropwise added under cooling with ice, then stirring was continued at room temperature for 2 hours. Subsequently the aqueous reaction mixture was extracted with 3 × 50 ml of ethyl acetate, the ethyl acetate extract was dried over sodium sulphate and evaporated in vacuo, yielding 6.7 g of crude product.

On subjecting the crude product to purification by preparative thin layer chromatography, with the use of a silica gel layer and a mixture of 70% ethyl acetate and 30 % n-heptane as running solvent, 4-(6-carbomethoxyhexyl)-5-hydroxymethyl-thiazole (XII, $R_1$ = H) of analytical purity was obtained.

IR spectrum (film): $\delta$ OH 3300, $\delta$ CH 2995–2860, $\delta$ C=O 1735, $\delta$ C-O 1250 cm$^{-1}$.

NMR spectrum (CCl$_4$): $\delta \leq$ CH (thiazole) 8.5 (1 H, s), $\delta$ CH$_2$(OH) 4.72 (2 H, s), $\delta$ OH 4.35 (1 H), $\delta$ OCH$_3$ 3.6 (3 H, s), $\delta$ CH $_2$ (vicinal to the ring) 2.65 (2 H, t, J = 7 Hz), $\delta$ CH$_2$(C=O) 2.22 (2 H, t, J = 7 Hz), $\delta$ CH$_2$ 1.9–1.1 (8 H, m) ppm.

h. 4-(6-carbomethoxyhexyl)-thiazole-5-carbaldehyde (XIII, $R_1$ = H)

The solution of 6.4 g of crude 4(6 -carbomethoxyhexyl)-5-hydroxymethylthiazole (XII, $R_1$ = H) in 60 ml of dichloromethane was dropwise added, under stirring, to the solution of 40 g of chromium trioxide-dipyridine complex in 800 ml of dichloromethane. Stirring of the reaction mixture was continued for 30 minutes, then the reaction mixture was filtered and the filtrate evaporated in vacuo. The evaporation residue was treated in 50 ml of hot methanol with charcoal, the filtered methanolic solution was evaporated, and the obtained 4.95 g of crude 4-(6-carbomethoxyhexyl)-thiazole-5carbaldehyde (XIII, $R_1$ = H) were recrystallized from diethyl ether. M.p.: 60–62° C.

IR spectrum (KBr): $\delta \leq$ CH 3090, $\delta$ CH 3000–2850, C=O 1730, 1660, $\delta$ C-O 1260 cm$^{-1}$.

NMR spectrum (CDCl$_3$): $\delta$ CHO 10.2 (1 H, s), $\delta \leq$ CH (thiazole)) 9.06 (1 H, s), $\delta$ OCH$_3$ 3.7 (3 H, s), $\delta$ CH$_2$ (vincinal to the ring) 3.2 (2 H, t, J = 7.5 Hz), $\delta$ CH$_2$(c=O) 2.35 (2 H, t, J = 7.5 Hz), $\delta$ CH$_2$ 2.05–1.1 (8 H, m) ppm. Mass spectrum: molecular weight 255. Mass number of the characteristic ion (m/e): 255, 226, 224, 182, 154, 140, 127, 126, 112, 99.

i. 4-(6-Carbomethoxyhexyl)-5-(3-keto-1-trans-octenyl)-thiazole (Ia, $R_1$ = H)

The solution of 4.8 g of 4-(6-carbomethoxyhexyl)-thiazole-5-carbaldehyde (XIII, $R_1$ = H) and 17.5 g of 2-oxoheptylidene triphenyl phosphorane in 25 ml of carbon tetrachloride was stirred under nitrogen current at room temperature for 16 hours. During this time the 4-(6-carbomethoxyhexyl)-thiazole-5-carbaldehyde (XIII, $R_1$ = H) completely converted into 4-(6-carbomethoxyhexyl)-5-(3-keto-1-trans-octenyl)-thiazole (Ia, $R_1$ = H). The latter compound was separated by column chromatography from the triphenyl phosphine oxide formed during the reaction and from the residual excess of 2-oxoheptylidene triphenyl phosphorane. A column prepared from 200 g of silicic acid was used for this separation. Elution was carried out with mixtures of n-heptane and ethyl acetate whose content of ethyl acetate was gradually increased. The product was eluted from the column with n-heptane containing 25% of ethyl acetate. In this way 5.2 g of 4-(6-carbomethoxyhexyl)-5-(3-keto-1-trans-octenyl)-thiazole of analytical purity (Ia, $R_1$ = H) were obtained.

IR spectrum (film): $\nu \leq CH$ 3080, $\nu$ CH 2095–2860, $\nu$ C=O 1735, 1685–1660, $\nu$ C=C 1595, $\nu$ C-O 1250 cm$^{-1}$.

NMR spectrum (CCl$_4$): $\delta \leq$ CH (thiazole) 8.55 (1 H, s), $\delta$ CH=CH 7.5, 6.3 (2 H, q J = 15 Hz), $\delta$ OCH$_3$ 3.55 (3 H, s), $\delta$ CH$_2$ (vicinal to the ring) 2.85 (2 H, t, J = 6 Hz), $\delta$ CH$_2$(C = O) 2.5 (2 H, t, J = 6 Hz), 2.2 (2 H, t, J = 6 Hz), $\delta$ CH$_2$ 1.95–1.1 (14 H, m), $\delta$ CH$_3$ 0.9 (3 H, t, J = 4 Hz) ppm.

Mass spectrum: moleculr weight 351.

Mass number of characteristic ions (m/e): 351, 320, 295, 280, 278, 252, 236, 223, 222, 208, 152, 138, 124.

EXAMPLE 2

Preparation of 4-(6-carbomethoxyhexyl)-5-(3-keto-1-trans-octenyl)-thiazole (Ia, $R_1$ = H)

2.9 g of 4-(6-carbomethoxyhexyl)-thiazole-5carboxylic acid chloride (XI, $R_1$ = H) obtained in the way described in point g) of Example 1 were dissolved in 25 ml of anhydrous tetrahydrofuran. To this solution cooled to −50° C a solution of 2.5 g of lithium-tri-tart-.butoxy-aluminum hydride in 10 ml of anhydrous tetrahydrofuran was added dropwise under stirring. The reaction mixture was stirred for an hour at −50° C, then allowed to take up room temperature and poured onto 100 ml of ice-water. The aqueous reaction mixture was extracted with 3 × 50 ml of diethylether, the extract dried over sodium sulphate and the solvent evaporated. The obtained 3 g of evaporation residue which contained 4-(6-carbomethoxyhexyl)-thiazole-5-carbaldehyde (XIII, $R_1$ = H) was purified by preparative thin layer chromatography, with the use of a silica gel layer as adsorbent and a mixture of 40% ethyl acetate and 60% n-heptane as running solvent. In this way 1.25 g of 4-(6-carbomethoxyhexyl)-thiazole-5-carbaldehyde (XIII, $R_1$ = H) described in point h) of Example 1 were obtained.

From 4-(6carbomethoxyhexyl)-thiazole-5-carbaldehyde (XIII, $R_1$ = H) 4-(6-carbomethoxyhexyl)-5-(3-keto-1-transoctenyl)-thiazole (Ia, $R_1$ = H) was prepared in the way specified in point i) of Example 1.

EXAMPLE 3

Preparation of 2-methyl-4-(6-carbomethoxyhexyl)-5-(3-keto-1-trans-octenyl)-thiazole (Ia, $R_1$ = CH$_3$)

a. 2-Methyl-4-(6-carbomethoxyhexyl)-thiazole-5-carboxylic acid methylester (VIII, $R_1$ = CH$_3$)

8.4 g of 9-carbomethoxy-2-chloro-3-ketonononic acid methylester (VI) and 2.5 g of thioacetamide (VII, $R_1$ = CH$_3$ were boiled in 50 ml of methanol for one hour, then methanol was evaporated in vacuo and the evaporation residue was dissolved in 75 ml of 2 N hydrochloric acid. The obtained solution was neutralized with a 5 % solution of sodium carbonate and saturated with ammonium sulphate, then extracted with 3 × 75 ml of diethyl ether. After drying the ethereal extract over sodium sulphate, it was evaporated in vacuo, affording 8.2 g of a crude product containing 2-methyl-4-(6-carbomethoxyhexyl)-thiazole-5-carboxylic acid methylester (VIII, $R_1$ = CH$_3$) which could be used without any further purification for the preparation of 2-methyl-4-(6-carboxyhexyl)-thiazole-5-carboxylic acid (IX, $R_1$ = CH$_3$) according to point (b) of this Example.

On purifying the crude product by preparative thin layer chromatography with the use of a silica gel layer as adsorbent and a mixture of 60% ethyl acetate and 40% n-heptane as running solvent, 2-methyl-4-(6-carbomethoxyhexyl)-thiazole-5-carboxylic acid methylester (VIII, $R_1$ = CH$_3$) of analytical purity was obtained.

IR spectrum (film): $\nu$ CH 3000–2860, $\nu$ C=O 1735, 1720, $\nu$ C-O 1270 cm$^{-1}$.

NMR spectrum (CCl$_4$): $\delta$ OCH$_3$ 3.82 (3 H, s), 3.6 (3 H, s) $\delta$ CH$_2$ (vicinal to the ring) 3.05 (2 H, t, J = 7 Hz), $\delta$ CH$_3$ 2.65 (3 H, s), $\delta$ CH$_2$(C=O) 2.25 (2 H, t, J = 7 Hz), $\delta$ CH$_2$ 1.95–1.15 (8 H, m) ppm.

b. 2-Methyl-4-(6-carboxyhexyl)-thiazole-5-carboxylic acid (IX, $R_1$ = CH$_3$)

The solution of 8 g of crude 2-methyl-4-(6-carbomethoxyhexyl)-thiazole-5-carboxylic acid methylester (VIII, $R_1$ = CH$_3$) in 25 ml of ethanol was treated with 40 ml of 2 N sodium hydroxide solution. The reaction mixture was refluxed for 30 minutes, then acidified with 5 N sulphuric acid under ice-cooling. After extracting the aqueous reaction mixture with 3 × 75 ml of ethyl acetate, the extract was dried over sodium sulphate and evaporated in vacuo. The obtained crude product was recrystallized from a mixture of acetone and n-hexane, affording 5.3 g of 2-methyl-4-(6-carboxyhexyl)-thiazole-5-carboxylic acid (IX, $R_1$ = CH$_3$). M.p.: 147–149° C.

IR spectrum (KBr): $\nu$ OH (carboxylic acid) 3300–2200, $\nu$ C=O 1685 cm$^{-1}$.

NMR spectrum (CDCl$_3$ + DMSO-d$_6$): $\delta$ COOH 9.0 (2 H), $\delta$ CH$_2$ (vicinal to the ring) 3.08 (2 H, t, J = 7 Hz), $\delta$ CH$_3$ 2.65 (3 H, s), $\delta$ CH$_2$(C=O) 2.25 (2 H, t, J = 7 Hz), $\delta$ CH$_2$ 1.95–1.1 (8 H, m) ppm.

c. 2-Methyl-4-(6-carbomethoxyhexyl)-thiazole-5-carboxylic acid (X, $R_1$ = CH$_3$)

5.15 g of 2-methyl-4-(6-carboxyhexyl)-thiazole-5-carboxylic acid (IX, $R_1$ = CH$_3$) and 5.4 g of p-toluenesulphonic acid monohydrate were dissolved in 200 ml of methanol. The reaction mixture was stirred for 2 hours at room temperature, then poured onto 500 ml of water. After saturating the aqueous solution with ammonium sulphate it was extracted with 3 × 200 ml of ethyl acetate, the ethyl acetate extract was washed with water, dried over sodium sulphate and evaporated in vacuo. Recrystallization of the obtained crude product from a mixture of diethyl ether and n-hexane afforded 4.3 g of 2-methyl-4-(6-carbomethoxyhexyl)-thiazole-5-carboxylic acid (X, $R_1$ = CH$_3$). M.p.: 106°–107° C. IR spectrum (KBr): $\nu$ OH (carboxylic acid) 3200–2200, $\nu$ C=O 1735, 1695, $\nu$ C-O 1235 cm$^{-1}$.

NMR spectrum (CDCl$_3$): $\delta$ COOH 11.45 (1 H), $\delta$ OCH$_3$ 3.65 (3 H, s), $\delta$ CH$_2$ (vicinal to the ring) 3.2 (2 H, t, J = 7.5 Hz), $\delta$ CH$_3$, 2.75 (3 H, s), $\delta$ CH$_2$(C=O) 2.25 (2 H, t, J = 7.5 Hz), $\delta$ CH$_2$ 2.0–1.05 (8 H, m) ppm.

d. 2-Methyl-4-(6-carbomethoxyhexyl)-5-hydroxymethyl-thiazole (XXI, $R_1$ = CH$_3$)

To the solution of 4.15 g of 2-methyl-4-(6-carbomethoxyhexyl)-thiazole-5-carboxylic acid (X, $R_1$ = CH$_3$) in 50 ml of anhydrous benzene 4.2 ml of oxalyl chloride were added dropwise, and the reaction mixture was allowed to stand overnight at room temperature, then benzene and excess oxalyl chloride were evaporated in vacuo. The obtained residue containing 2-methyl-4-(6-carbomethoxyhexyl)-thiazole-5-carboxylic acid chloride (XI, $R_1$ = CH$_3$) was dissolved in 20 ml of anhydrous dioxane, and a suspension of 1.1 g of sodium borohydride in 20 ml of anhydrous dioxane was added dropwise to the solution under continuous stirring. Stirring of the reaction mixture was continued for 30 minutes at room temperature and for further 60 minutes at 80° C.

When the reaction mixture was cooled to room temperature, 25 ml of water were dropwise added under ice-cooling to the reaction mixture, and stirring was continued for 2 hours at room temperature. Subsequently, the aqueous reaction mixture was extracted with 3 × 50 ml of ethyl acetate. The ethyl acetate extract was dried over sodium sulphate and evaporated in vacuo, yielding 2.95 of crude product.

On purifying the crude product by preparative thin layer chromatography, using a silica gel layer as adsorbent and a mixture of 70% ethyl acetate and 30% n-heptane as running solvent, 2-methyl-4-(6-carbomethoxyhexyl)-5-hydroxymethyl-thiazole (XII, $R_1$ = $CH_3$) of analytical purity was obtained.

Ir spectrum (film): $\nu$ OH 3300, $\nu$ CH 3000–2860, $\nu$ C=O 1735, $\nu$ C-O 1255, $\nu$ C-O (H) 1020 cm$^{-1}$.

NMR spectrum (CCl$_4$); $\delta$ CH$_2$ (OH) 4.62 (2 H, s), $\delta$ OH 4.22 (1 H), $\delta$ OCH$_3$ 3.62 (3 H, s), $\delta$ CH$_3$ 2.6 (3 H, s), $\delta$ CH$_2$ (vicinal to the ring) 2.59 (2 H, t, J = 7.5 Hz), $\delta$ CH$_2$ (C=O) 2.25 (2 H, t, J = 7 Hz), $\delta$ CH$_2$ 1.95–1.1 (8 H, m) ppm.

e. 2-Methyl-4-(6-carbomethoxyhexyl)-thiazole-5-carbaldehyde (XIII, $R_1$ = $CH_3$)

The solution of 2.8 g of crude 2-methyl-4-(6-carbomethoxyhexyl)-5-hydroxymethyl thiazole (XII, $R_1$ = $CH_3$) in 25 ml of dichloromethane was dropwise added to the solution of 16 g of chromium trioxide-dipyiridine complex in 320 ml of dichloromethane. Stirring of the reaction mixture was continued for 30 minutes, then the reaction mixture was filtered and the filtrate was evaporated in vacuo. After purifying the crude product obtained as evaporation residue, by preparative thin layer chromatography using a silica gel layer as adsorbent and a mixture of 50% ethyl acetate and 50% of n-heptane as running solvent, 2.15 g of 2-methyl-4-(6-carbomethoxyhexyl)-thiazole-5-carbaldehyde (XIII, $R_1$ = $CH_3$) were obtained.

Ir spectrum (film): $\nu$ CH 2995–2860, $\nu$ C=O 1732, 1660, $\nu$ C-O 1255 cm$^{-1}$.

NMR spectrum (CCl$_4$): $\delta$CHO 10.0 (1 H, s), $\delta$ OCH$_3$ 3.61 (3 H, s), $\delta$ CH$_2$(vicinal to the ring) 3.0 (2 H, t, J = 7.5 Hz), $\delta$ CH$_3$ 2.7 (3 H, s), $\nu$ CH$_2$(c=O) 2.25 (2 H, t, J = 7 Hz), $\delta$ CH$_2$ 1.95–1.1 (8 H, m) ppm. Mass spectrum: molecular weight 269. Mass number of characteristic ions (m/e): 269, 240, 238, 196, 168, 154, 141, 113.

f. 2-Methyl-4-(6-carbomethoxyhexyl)-5-(3-keto-1-trans-octenyl)-thiazole (Ia, $R_1$ = $CH_3$)

2 g of 2-methyl-4-(6-carbomethoxyhexyl)-thiazole-5-carbaldehyde (XIII, $R_1$ = $CH_3$) and 7 g of 2-oxoheptylidenetriphenyl phosphorane were dissolved in 15 ml of carbon tetrachloride. The reaction mixture was stirred for 16 hours under nitrogen current. During this time the 2-methyl-4-(6-carbomethoxyhexyl)-thiazole-5-carbaldehyde (XIII, $R_1$ = $CH_3$) was completely converted into 2-methyl-4-(6-carbomethoxyhexyl)-5-(3-keto-1-trans-octenyl)-thiazole (Ia, $R_1$ = $CH_3$). The latter compound was separated by preparative thin layer chromatography from the triphenyl phosphine oxide formed during the reaction and from the residual excess of 2-oxoheptylidene triphenyl phosphorane. For the separation a silica gel layer was used as adsorbent and a mixture of 50% ethyl acetate and 50% n-heptane as running solvent. In this way 2.1 g of 2-methyl-4-(6-carbomethoxyhexyl)-5-(3-keto-1-trans-octenyl)-thiazole (Ia, $R_1$ = $CH_3$) were obtained.

Ir spectrum (film): $\nu$ CH 3000–2860, $\nu$ C=O 1735, 1685–1660, $\nu$ C=C 1592, $\nu$ C-O 1250 cm$^{-1}$.

NMR spectrum (CCl$_4$): $\delta$ CH=CH 7.52, 6.22 (2 H, q, J = 15.5 Hz), $\delta$ OCH$_3$ 3.61 (3 H, s), $\delta$ CH$_2$(vicinal to the ring) 2.78 (2 H, t, J = 6.5 Hz), $\delta$ CH$_3$ 2.63 (3 H, s), $\delta$ CH$_2$(C=O) 2.5 (2 H, t, J = 7 Hz), 2.25 (2 H, t, J = 7 Hz), $\delta$ CH$_2$ 1.95–1.1 (14 H, m) $\delta$ CH$_3$ 0.95 (3 H, t, J = 6 Hz) ppm. Mass spectrum: molecular weight 365. Mass number of characteristic ions (m/e): 365, 334, 309, 294, 292, 266, 250, 237, 236, 222, 166, 152, 138.

EXAMPLE 4

Preparation of 2-methyl-4-(6-carbomethoxyhexyl)-5-(3-keto-1-trans-octenyl)-thiazole (Ia, $R_1$ = $CH_3$)

To a suspension of 0.45 g of sodium hydride in 5 ml of anhydrous 1,2-dimethoxy-ethane a solution of 4.12 g of 2-oxoheptylphosphonic acid dimethyl ester in 20 ml of 1,2-dimethoxy-ethane was added under stirring at room temperature. The reaction mixture was stirred for an hour, then a solution of 1 g of 2-methyl-4-(6-carbomethoxyhexyl)-thiazole-5-carbaldehyde (XIII, $R_1$ = $CH_3$) prepared according to point (e) of Example 2, in 10 ml of 1,2-dimethoxy-ethane was added dropwise, and stirring was continued for 5 hours. After adding dropwise 30 ml of water under ice-cooling to the reaction mixture, it was extracted with 3 × 20 ml of diethyl ether. The extract was dried on over sodium sulphate and evaporated in vacuo. The evaporation residue was purified by preparative thin layer chromatography, using a silica gel layer as adsorbent and a mixture of 40% ethyl acetate and 60% n-heptane as running solvent. The yield was 0.81 g of 2-methyl-4-(6-carbomethoxyhexyl)-5-(3-keto-1-trans-octenyl)-thiazole (Ia, $R_1$ = $CH_3$) of chromatographic purity.

EXAMPLE 5

Preparation of 4-(6-carboxyhexyl)-5-(3-keto-1-transoctenyl)-thiazole (Ib, $R_1$ = H)

To a suspension of 2.65 g of 4-(6-carbomethoxyhexyl)-5-(3-keto-1-trans-octenyl)-thiazole (Ia, $R_1$ = H) in 50 ml of a 0.2 M phosphate buffer of pH 7.5, 265 mg of lipase enzyme of an activity of 40 U/mg, prepared with the fungus Rhizopus oryzae, 26 mg of the sodium salt of taurocholic acid, and 2.6 ml of a 10 % solution of gum arabic were added. The mixture was then shaken at 25° C in a screening shaker desk at 260 revolutions/minute and an amplitude of 2 cm for 24 hours. Then the reaction mixture was diluted with 100 ml of water, acidified with citric acid and extracted with 3 × 75 ml of ethyl acetate. The ethyl acetate extract was dried over sodium sulphate and evaporated in vacuo. The obtained 2.95 g of evaporation residue were purified by chromatography on a column prepared with 100 g of silicic acid, eluting with mixtures of n-heptane and ethyl acetate whose ethyl acetate content was gradually increased. 4-(6-Carboxyhexyl)-5-(3-keto-1-trans-octenyl)-thiazole (Ib, $R_1$ = H) was eluted from the column by a mixture consisting of 60% ethyl acetate and 40 % n-heptane, affording thus 1.8 g of a product of chromatographic purity which was recrystallized from acetone. M.p.: 67°–68° C. IR spectrum (KRr): $\nu$ OH (carboxylic acid) 3200–2300, $\nu \leq$ CH 3095, $\nu$ CH 3000–2860, $\nu$ C-O 1713, 1690, $\nu$ C=C 1590 cm$^{-1}$.

NMR spectrum (CDCl$_3$): $\delta$ COOH 10.9 (1 H), $\delta \leq$ CH (thiazole) 8.8 (1H, s), $\delta$ CH=CH 7.72, 6.52 (2 H, q, J = 15.5 Hz), $\delta$ CH$_2$(vicinal to the ring) 2.9 (2 H, t, J = 7 Hz), $\delta$ CH$_2$(c=O) 2.65 (2 H, t, J = 7 Hz), 2.32 (2 H, t, J = 7 Hz), δ CH$_2$ 2.05–1.1 (14 H, m), δ CH$_3$ 0.88 (3 H, t, J = 6 Hz) ppm. Mass spectrum: molecular weight 337. Mass numger of characteristic ions (m/e): 337, 281, 278, 266, 238, 236, 223, 208, 152.

EXAMPLE 6

Preparation of 4-(6-carboxyhexyl)-5-(3-keto-1-trans-octenyl)-thiazole (Ib, R$_1$ = H)

2 ml of 1 N sodium hydroxide was dropwise added under nitrogen atmosphere and under ice-cooling to a solution of 175 mg of 4-(6-carbomethoxyhexyl)-5-(3-keto-1-trans-octenyl)-thiazole (Ia, R$_1$ = H) in 5 ml of ethanol. The solution was subsequently stirred for 1.5 hours at room temperature. Then the reaction mixture was poured onto 30 ml of icewater, acidified with 1 N hydrochloric acid and extracted with 3 × 15 ml of ethyl acetate. The ethyl acetate extract was dried over sodium sulphate and evaporated in vacuo. The evaporation residue was purified by preparative thin layer chromatography, using a silica gel layer as adsorbent and the organic phase of a mixture of 110 ml of ethyl acetate, 50 ml of n-heptane, 100 ml of water and 20 ml of acetic acid as running solvent. In this way 71 mg of 4-(6-carboxyhexyl)-5-(3-keto-1-trans-octenyl)-thiazole (Ib, R$_1$ = H) of chromatographic purity were obtained. The m.p. and spectroscopical data of the product agreed with those specified in Example 5.

EXAMPLE 7

Preparation of 2-methyl-4-(6-carboxyhexyl)-5-(3-keto-1-trans-octenyl)-thiazole (Ib, R$_1$ = CH$_3$)

To a suspension of 912 mg of 2-methyl-4-(6-carbomethoxyhexyl)-5-(3-keto-1-trans-octenyl)-thiazole (Ia, R$_1$ = CH$_3$) in 20 ml of 0.2 M phosphate buffer of pH 7.5, 90 mg of the lipase enzyme specified in Example 5, 9 mg of the sodium salt of taurocholic acid nd 0.9 ml of a 10 % solution of gum arabic were added. The mixture was then shaken at 25° C in a screening shaker desk at 260 revolutions/minute and an amplitude of 2 cm for 24 hours. Then the reaction mixture was diluted with 50 ml of water, acidified with citric acid and extracted with 3 × 40 ml of ethyl acetate. The ethyl acetate extract was dried over sodium sulphate and evaporated in vacuo. The obtained 1.03 g of evaporation residue were purified by preparative thin layer chromatography in the way specified in Example 6. Thus, 645 mg of 2-methyl-4-(6-carboxyhexyl)-5-(3-keto-1-trans-octenyl)-thiazole Ib, R$_1$ = CH$_3$) were obtained.

IR spectrum (film): ν OH (carboxylic acid) 3500–2400, ν CH 2995–2860, νC=O 1720, 1680, νC=C 1590 cm$^{-1}$.

NMR spectrum (CCl$_4$): δ COOH 10.4 (1 H), δCH=CH 7.45, 6.18 (2 H, q, J = 15.5 Hz), δ CH$_2$ (vicinal to the ring) 2.75 (2 H, t, J = 7 Hz), δCH$_3$ 2.65 (3 H, s), δCH$_2$(C=O) 2.45 (2 H, t, J = 7 Hz), 2.25 (2 H, t, J = 7 Hz), δCH$_2$ 1.95–1.1 (14 H, m), δCH$_3$ 0.9 (3 H, t, J = 5 Hz) ppm. Mass spectrum: molecular weight 351. Mass number of characteristic ions (m/e): 351, 295, 292, 280, 252, 250, 237, 222, 166.

EXAMPLE 8

Preparation of 4-(6-carbomethoxyhexyl)-5-(3-hydroxy-1-trans-octenyl)-thiazole (Ic, R$_1$ = H)

The solution of 143 mg of sodium borohydride in 30 ml of water was added to the solution of 2.65 g of 4-(6-carbomethoxyhexyl)-5-(3-keto-1-trans-octenyl)-thiazole (Ia, R$_1$ = H) in 30 ml of isopropanol. The obtained reaction mixture was stirred for 2 hours at room temperature, then poured onto 150 ml of water, and extracted with 3 × 75 ml of ethyl acetate. The ethyl acetate extract was washed with water to neutral and evaporated in vacuo. The obtained 2.5 g of evaporation residue was subjected to chromatography on a column prepared with 100 g of silicic acid, the elution was carried out with mixtures of n-heptane and ethyl acetate of gradually increasing ethyl acetate content. The desired 4-(6-carbomethoxyhexyl)-5-(3-hydroxy-1-trans-octenyl-thiazole, (Ic, R$_1$ = H) was eluted from the column with a mixture consisting of 70% n-heptane and 30% ethyl acetate, affording 2.2 g of a product of chromatographic purity.

IR spectrum (film): νOH 3350, ν≦CH 3080, νCH 3000–2860, νC=O 1735, νC=C 1640, νC=O 1250 cm$^{-1}$.

NMR spectrum (CCl$_4$): δ≦CH (thiazole) 8.5 (1 H, s), δCH=CH 6.67 (1 H, d, J = 16 Hz), 5.97 (1 H, dd, J = 16 Hz, J = 6 Hz), δCH(OH) 4.2 (1 H, m), δOCH$_3$ 3.6 (3 H, s), δOH 3.12 (1 H), δCH$_2$(vicinal to the ring) 2.75 (2 H, t, J = 7 Hz), δCH$_2$(C=O) 2.25 (2 H, t, J = 7 Hz), δCH$_2$ 1.95–1.1 (16 H, m), δCH$_3$ 0.9 (3 H, t, J = 5 Hz) ppm. Mass spectrum: molecular weight 353. Mass number of characteristic ions (m/e): 353, 322, 282, 280, 254, 250, 238, 222, 124.

EXAMPLE 9

Preparation of 2-methyl-4-(6-carbomethoxyhexyl)-5-(3-hydroxy-1-trans-octenyl)-thiazole (Ic, R$_1$ = CH$_3$)

The solution of 47 mg of sodium borohydride in 10 ml of water was added to the solution of 912 mg of 2-methyl-4-(6-carbomethoxyhexyl)-5-(3-keto-1-trans-octenyl)-thiazole (Ia, R$_1$ = CH$_3$) in 10 ml of isopropanol. The obtained reaction mixture was stirred for 2 hours at room temperature, then poured onto 50 ml of water and extracted with 3 × 25 ml of ethyl acetate. The ethyl acetate extract was washed with water to neutral, dried over sodium sulphate and evaporated in vacuo. The obtained 830 mg of evaporation residue was purified by preparative thin layer chromatography, using a silica gel layer as adsorbent and a mixture of 50% ethyl acetate and 50% n-heptane as running solvent. Thus, 705 mg of 2-methyl-4-(6-carbomethoxyhexyl)-5-(3-hydroxy-1-trans-octenyl-thiazole (Ic, R$_1$ = CH$_3$) of chromatography purity were obtained.

IR spectrum (film): νOH 3350, νCH 3000–2860, νC=O 1740, νC=C 1640, νC-O 1255 cm$^{31\ 1}$.

NMR spectrum (CCl$_4$): δCH=CH 6.48 (1 H, d, J = 15 Hz), 5.7 (1 H, dd, J = 15 Hz, J = 5.5 Hz), δCH(OH) 4.06 (1 H, m), δOCH$_3$ 3.56 (3H, s), δOH 3.0 (1 H), δCH$_3$ + δCH$_2$ (vicinal to the ring) 2.55 (5 H), δCH$_2$(C=O) 2.22 (2 H, t, J = 6.5 Hz), δCH$_2$ 1.95–1.05 (16 H, m), δCH$_3$ 0.9 (3 H, t, J = 5 Hz) ppm. Mass spectrum: molecular weight 367. Mass number of characteristic ions (m/e): 367, 336, 296, 294, 268, 264, 252, 239, 236, 196, 183, 140.

EXAMPLE 10

Preparation of 4-(6-carboxyhexyl)-5-(3-hydroxy-1-trans-octenyl)-thiazole (Id, $R_1$ = H)

To the suspension of 1.75 g of 4-(6-carbomethoxyhexyl)-5-(3-hydroxy-1-trans-octenyl)-thiazole (Ic, $R_1$ = H) in 35 ml of a 0.2 M phosphate buffer of pH 7.5, 175 mg of the lipase enzyme specified in Example 5, 17.5 mg of the sodium salt of taurocholic acid and 1.75 ml of a 10% solution of gum arabic were added. The mixture was then shaken at 25° C in a screening shaker desk at 260 revolutions/minute and an amplitude of 2 cm for 24 hours, whereafter the reaction mixture was diluted with 100 ml of water, acidified with citric acid and extracted with 3 × 70 ml of ethyl acetate. The ethyl acetate extract was dried over sodium sulphate and evaporated in vacuo. The obtained 1.95 g of evaporation residue was purified by chromatography on a column prepared with 50 g of silicic acid, using mixtures of n-heptane and ethyl acetate whose ethyl acetate content was gradually increased, as the eluting solvent. 4-(6-Carboxyhexyl)-5-(3-hydroxy-1-trans-octenyl)-thiazole (ID, $R_1$ = H) was eluted from the column by a mixture consisting of 70% ethyl acetate and 30% n-heptane. Thus, 1.25 g of a product of chromatographic purity was obtained which was recrystallized from a mixture of diethyl ether and n-hexane.

M.p.: 73°-74° C.

IR spectrum (film): $\nu$OH 3500-2300, $\nu$CH 3000-2860, $\nu$C=O 1710, $\nu$C=C 1635 cm$^{-1}$.

NMR spectrum (CDCl$_3$): $\delta \leq$ CH (thiazole) 8.55 (1 H s), $\delta$OH 6.65 (2 H), $\delta$CH=CH 6.65 (1 H, d, J = 15 Hz), 5.9 (1 H, dd, J = 15 Hz, J = 6 Hz), $\delta$CH(OH) 4.22 (1 H, m), $\delta$CH$_2$ (vicinal to the ring) 2.75 (2 H, t, J = 6 Hz), $\delta$CH$_2$(C=O) 2.28 (2 H, t, J = 6 Hz), $\delta$CH$_2$ 1.95-1.05 (16 H, m), $\delta$CH$_3$ 0.87 (3 H, t, J = 4 Hz) ppm. Mass spectrum: molecular weight 339. Mass number of characteristic ions (m/e): 339, 321, 280, 268, 250, 240, 238, 225, 222, 182, 169, 152, 126, 124.

Example 11

Preparation of 2-methyl-4-(6-carboxyhexyl)-5-(3-hydroxy-1-trans-octenyl)-thiazole (Id, $R_1$ = CH$_3$)

The solution of 76 mg of sodium borohydride in 6 ml of water was added to the solution of 351 mg of 2-methyl-4-(6-carboxyhexyl)-5-(3-keto-1-trans-octenyl)-thiazole (Ib, $R_1$ = CH$_3$) in 4 ml of isopropanol. The reaction mixture was allowed to stand overnight at room temperature, then diluted with 50 ml of water, acidified with 1 N hydrochloric acid and extracted with 3 × 25 ml of ethyl acetate. The ethyl acetate extract was dried over sodium sulphate and evaporated in vacuo. The obtained 317 mg of evaporation residue was purified by preparative thin layer chromatography in the way specified in Example 6. Thus, 245 mg of 2-methyl-4-(6-carboxyhexyl)-5-(3-hydroxy-1-trans-octenyl)-thiazole (Id, $R_1$ = CH$_3$) were obtained. IR spectrum (film): $\nu$ OH 3500-2300, $\nu$ CH 3000-2860, $\nu$ C=O 1710, $\nu$ C=C 1640 cm$^{-1}$.

NMR spectrum (CDCl$_3$): $\delta$OH 7.15 (2 H), $\delta$CH=CH 6.55 (1 H, d, J = 15 Hz), 5.78 (1 H, dd, J = 15 Hz, J = 6 Hz), $\delta$CH(OH) 4.20 (1 H, m), $\delta$CH$_3$ + $\delta$CH$_2$ (vicinal to the ring), 2.62 (5 H, m), $\delta$CH$_2$(C=O) 2.28 (2 H, t, G = 6 Hz), $\delta$CH$_2$ 1.9-1.05 (16 H, m), $\delta$CH$_3$ 0.9 (3 H, t, J = 5 Hz) ppm. Mass spectrum: molecular weight 353. Mass number of characteristic ions (m/e): 353, 335, 294, 282, 264, 254, 252, 239, 236, 196, 183, 140.

EXAMPLE 12

Preparation of 4-(6-carbomethoxyhexyl)-5-(3-acetoxy-1-trans-octenyl)-thiazole (Ie, $R_1$ = H)

To the solution of 353 mg of 4-(6-carbomethoxyhexyl)-5-(3-hydroxy-1-trans-octenyl)-thiazole (Ic, $R_1$ = H) in 4 ml of anhydrous pyridine, 1 ml of acetic anhydride was added. The reaction mixture was allowed to stand for 24 hours at room temperature, diluted with 50 ml of water and extracted with 3 × 15 ml of ethyl acetate. The ethyl acetate extract was washed with water, dried over sodium sulphate and evaporated under vacuum in vacuo. The obtained 390 mg of evaporation residue was purified by preparative thin layer chromatography, using a silica gel layer as adsorbent and a mixture of 40% ethyl acetate and 60% n-heptane as running solvent. Thus, 285 mg of 4-(6-carbomethoxyhexyl)-5-(3-acetoxy-1-trans-octenyl)-thiazole (Ie, $R_1$ = H) of chromatographic purity were obtained.

IR spectrum (film): $\nu \leq$ CH 3080, $\nu$CH 3000-2860, $\nu$C=O 1735, $\nu$C=C 1642, $\nu$C-O 1240 cm$^{-1}$.

NMR spectrum (CDCl$_3$): $\delta \leq$ CH (thiazole) 8.46 (1 H, s), $\delta$CH=CH 6.71 (1 H, d, J = 15 Hz), 5.76 (1 H, dd, J = 15 Hz, J = 6 Hz), $\delta$CH(OAc) 5.35 (1 H, m), $\delta$OCH$_3$ 3.6 (3 H, s), $\delta$CH$_2$ (vicinal to the ring) 2.75 (2 H, t, J = 7 Hz), $\delta$CH$_2$(C=O) 2.25 (2 H, t, J = 6 Hz), $\delta$CH$_3$(C=O) 2.0 (3 H, s), $\delta$CH$_2$ 1.9-1.1 (16 H, m), $\delta$CH$_3$ 0.9 (3 H, t, J = 5 Hz) ppm. Mass spectrum: molecular weight 395. Mass number of characteristic ions (m/e): 395, 353, 352, 336, 335, 324, 282, 280, 267, 254, 250, 222.

EXAMPLE 13

Preparation of 2-methyl-4-(6-carbomethoxyhexyl)-5-(3-acetoxy-1-trans-octenyl)-thioazole (Ie, $R_1$ = CH$_3$)

To the solution of 367 mg of 2-methyl-4-(6-carbomethoxy-hexyl)-5-(3-hydroxy-1-trans-octenyl)-thiazole (Ic, $R_1$ = CH$_3$) in 4 ml of anhydrous pyridine, 1 ml of acetic anhydride was added. The reaction mixture was allowed to stand for 24 hours at room temperature, diluted with 50 ml of water and extracted with 3 × 15 ml of ethyl acetate. The ethyl acetate extract was washed with water, dried over sodium sulphate and evaporated in vacuo. The obtained 403 mg of evaporation residue was purified by preparative thin layer chromatography, using a silica gel layer as adsorbent and a mixture of 40 % ethyl acetate and 60 % n-heptane as running solvent. Thus, 290 mg of 2-methyl-4-(6-carbomethoxyhexyl)-5-(3-acetoxy-1-trans-octenyl)-thiazole (Ie, $R_1$ = CH$_3$) of chromatographic purity were obtained.

IR spectrum (film): $\nu$CH 3000-2860, $\nu$C=O 1735, $\nu$C=C 1640, $\nu$C-O 1240 cm$^{-1}$.

NMR spectrum (CDCl$_3$): $\delta$CH=CH 6.55 (1 H, d, J = 15 Hz), 5.60 (1 H, dd, J = 15 Hz, J = 6 Hz), $\delta$CH(OAc) 5.3 (1 H, m), $\delta$OCH$_3$ 3.6 (3 H, s), $\delta$CH$_2$ (vicinal to the ring) 2.65 (2 H, t, J = 7 Hz), $\delta$CH$_3$ 2.6 (3 H, s) $\delta$CH$_2$(C=O) 2.3 (2 H, t, J = 7 Hz), $\delta$CH$_3$(C=O) 2.05 (3 H, s), $\delta$CH$_2$ 1.9-1.05 (16 H, m), $\delta$CH$_3$ 0.9 (3 H, t, J = 5 Hz) ppm. Mass spectrum: molecular weight 409. Mass number of characteristic ions (m/e): 409, 378, 367, 366, 350, 349, 338, 336, 296, 294, 281, 268, 238. What we claim is:

1. A thiazole derivative of the formula

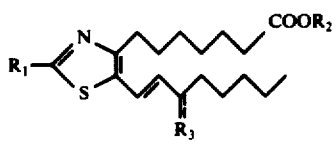

wherein $R_1$ and $R_2$ are hydrogen or methyl and $R_3$ is oxo, hydroxyl or acetoxy.

2. A process for the production of thiazole derivatives of the formula

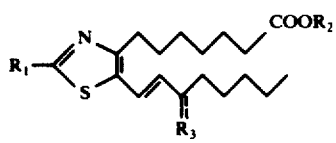

wherein $R_1$ and $R_2$ are hydrogen or methyl and $R_3$ is oxo, hydroxyl or acetoxy, comprising the steps of reacting the sodium derivative of an acetoacetic acid methylester of the formula $CH_3COCH_2COOR_4$ wherein $R_4$ is methyl, with a 7-carbomethoxyheptanoyl chloride of the formula $R_5OOC(CH_2)_6COCl$, wherein $R_5$ is methyl, and converting the obtained 10-carbomethoxy-2,4-diketodecane-3-carboxylic acid methylester of the formula

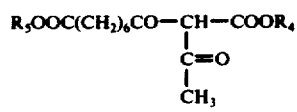

wherein $R_4$ and $R_5$ have the same meanings as above, with sodium methylate into 9-carbomethoxy-3-ketononanoic acid methylester of the formula $CH_3OOC(CH_2)_6CO\text{-}CH_2\text{-}COOCH_3$ halogenating the latter compound to 9-carbomethoxy-2-halo-3-ketononanoic acid methylester of the formula $CH_3OOC(CH_2)_6CO\text{-}CHY\text{-}COOCH_3$ wherein Y is halogen, reacting the last-named compound with a thioacid amide of the formula

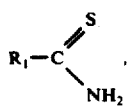

wherein $R_1$ is hydrogen of methyl, hydrolyzing the obtained 4-(6-carbomethoxyhexyl)-thiazole-5-carboxylic acid methylester of the formula

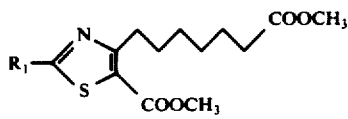

wherein $R_1$ is hydrogen or methyl, to obtain 4-(6-carboxyhexyl)-thiazole-5-carboxylic acid of the formula

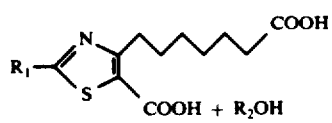

wherein $R_1$ is hydrogen or methyl, subjecting the last-named compound to selective esterification with an alcohol of the formula $R_2OH$, wherein $R_2$ is methyl, in the presence of p-toluenesulphonic acid, converting the thus-obtained 4-(6-carbomethoxyhexyl)-thiazole-5-carboxylic acid of the formula

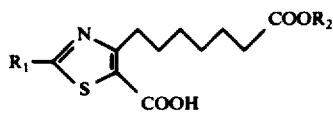

wherein $R_1$ is hydrogen or methyl and $R_2$ is methyl, into 4-(6-carbomethoxyhexyl)-thiazole-5-carboxylic chloride of the formula

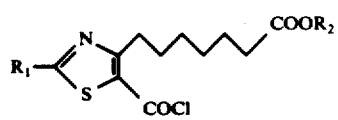

wherein $R_1$ is hydrogen or methyl and $R_2$ is methyl, reducing the last-named compound with an alkali metal borohydride to 4-(6-carbomethoxyhexyl)-5-hydroxymethyl-thiazole of the formula

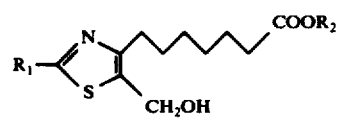

wherein $R_1$ is hydrogen or methyl and $R_2$ is methyl, then oxidizing the last-named compound to 4-(6-carbomethoxyhexyl)-thiazole-5-carbaldehyde of the formula

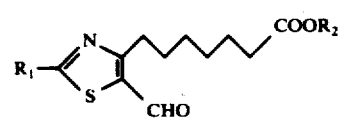

wherein $R_1$ is hydrogen or methyl and $R_2$ is methyl, reacting the last-named compound with 2-oxo-heptylidene-triphenyl phosphorane to obtain 4-(6-carbomethoxyhexyl)-5-(3-keto-1-trans-octenyl)-thiazole of the formula

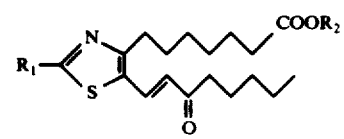

wherein $R_1$ is hydrogen or methyl and $R_2$ is methyl.

3. A process for the production of thiazole derivatives of the formula

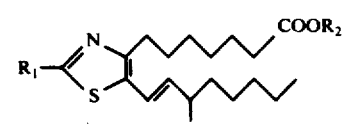

wherein $R_1$ and $R_2$ are hydrogen or methyl and $R_3$ is oxo, hydroxyl or acetoxy, comprising the steps of reducing 4-(6-carbomethoxyhexyl)-thiazole-5-carboxylic chloride of the formula

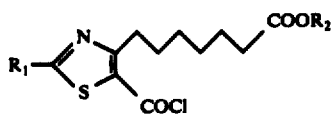

wherein R₁ is hydrogen or methyl and R₂ is methyl, with lithium tri-tert.-butoxy-aluminium hydride to 4-(6-carbomethoxyhexyl)-thiazole-5-carbaldehyde of the formula

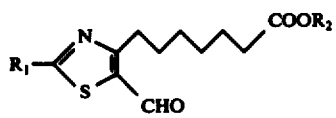

wherein R₁ is hydrogen or methyl and R₂ is methyl, then reacting the last-named compound with 2-oxo-heptylidene-triphenyl phosphorane to obtain 4-(6-carbomethoxyhexyl)-5-(3-keto-1-trans-octenyl)-thiazole of the formula

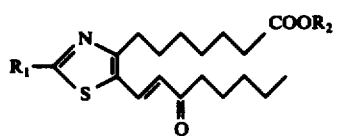

wherein R₁ is hydrogen or methyl and R₂ is methyl.

4. A process for the production of thiazole derivatives of the formula

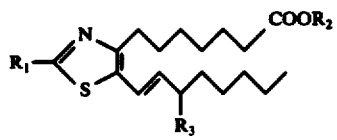

wherein R₁ and R₂ are hydrogen or methyl and R₃ is oxo, hydroxyl or acetoxy, comprising converting 4-(6-carbomethoxyhexyl)-thiazole-5-carbaldehyde of the formula

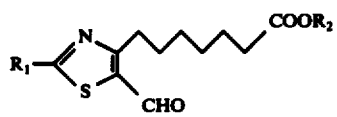

wherein R₁ is hydrogen or methyl and R₂ is methyl, with the sodium derivative of 2-oxoheptylphosphonic acid dimethylester or with 2-oxo-heptylidenetriphenyl phosphorane into 4-(6-carbomethoxyhexyl)-5-(3-keto-1-trans-octenyl)-thiazole of the formula

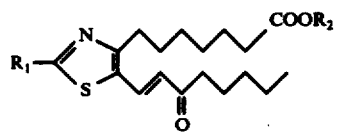

wherein R₁ is hydrogen or methyl and R₂ is methyl.

5. A process as claimed in claim 4, and hydrolyzing the last-named compound to 4-(6-carboxy-hexyl)-5-(3-keto-1-trans-octenyl)-thiazole of the formula

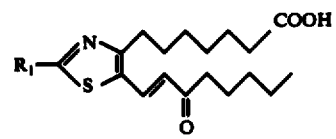

wherein R₁ is hydrogen or methyl.

6. A process as claimed in claim 5, and reducing the last-named compound with an alkali metal borohydride to 4-(6carboxyhexyl)-5-(3-hydroxy-1-trans-octenyl)-thiazole of the formula

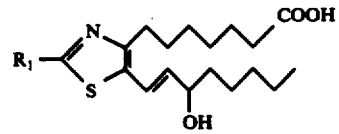

wherein R₁ is hydrogen or methyl.

7. A process as claimed in claim 4, and reducing the last-named compound with an alkali metal borohydride to 4-(6carbomethoxyhexyl)-5-(3-hydroxy-1-trans-octenyl)-thiazole of the formula

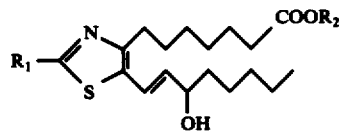

wherein R₁ is hydrogen or methyl and R₂ is methyl.

8. A process as claimed in claim 7, and hydrolyzing the last-named compound to 4-(6-carboxyhexyl)-5-(3-hydroxy-1-trans-octenyl)-thiazole of the formula

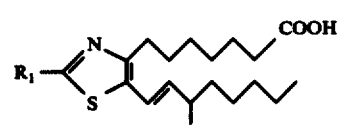

wherein R₁ is hydrogen or methyl.

9. A process as claimed in claim 7, and acylating the last-named compound with acetic acid to 4-(6carbomethoxyhexyl)-5-(3-acetoxy-1-transoctenyl)-thiazole of the formula

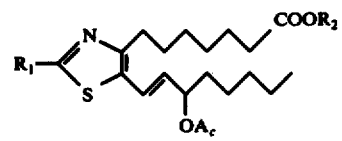

wherein R₁ is hydrogen or methyl and R₂ is methyl.

10. A process as claimed in claim 2, and carrying out the chlorination of 9-carbomethoxy-3-ketononanoic acid methylester with sulphuryl chloride.

11. A process as claimed in claim 2, and carrying out the hydrolysis of 4-(6-carbomethoxyhexyl)-thiazole-5-carboxylic acid with an alkali hydroxide.

12. A process as claimed in claim 2, and carrying out the oxidation of 4-(6-carbomethoxyhexyl)-5-hydroxymethylthiazole with a chromium trioxide-dipyridine complex.

13. A process as claimed in claim 4, and carrying out the hydrolysis of the ester group of the last-named compound with an esterase enzyme.

14. A process as claimed in claim 8, and carrying out the hydrolysis of the ester group of the last-named compound with an esterase enzyme.

* * * * *